United States Patent [19]
Yoo

[11] 3,991,119
[45] Nov. 9, 1976

[54] HYDROFORMYLATION OVER COBALT ON SUPPORT COMPRISING SEPARATE ALUMINA PHASE

[75] Inventor: Jin Sun Yoo, South Holland, Ill.

[73] Assignee: Atlantic Richfield Company, Los Angeles, Calif.

[22] Filed: Feb. 24, 1975

[21] Appl. No.: 552,008

Related U.S. Application Data

[63] Continuation of Ser. No. 20,422, March 17, 1970, abandoned.

[52] U.S. Cl. .......................................... 260/604 HF
[51] Int. Cl.² .......................................... C07C 45/04
[58] Field of Search ............................... 260/604 HF

[56] References Cited
UNITED STATES PATENTS 3,239,569  3/1966  Slaugh et al. ................. 260/604 HF 3,880,938  4/1975  Massie .......................... 260/604 HF

OTHER PUBLICATIONS

Tucci, E. R., I & E C Product Res. and Dev., vol. 7, pp. 32–38, 1968.
Rudkovskii et al., Chem. Abstr., vol. 57, 10105b, 1962.

*Primary Examiner*—James O. Thomas, Jr.
*Assistant Examiner*—W. B. Lone
*Attorney, Agent, or Firm*—John R. Ewbank

[57] ABSTRACT

A new, solid catalyst suitable for the hydroformylation of low molecular weight olefins is disclosed. The catalyst composition is a hydrido-cobalt or nickel carbonyl-Group VA electron donor ligand complex on a solid, acidic, silica-based support. Preferred electron donor ligands are phosphines and tertiary amines. A preferred catalyst support contains amorphous silica-alumina and alumina.

4 Claims, No Drawings

HYDROFORMYLATION OVER COBALT ON SUPPORT COMPRISING SEPARATE ALUMINA PHASE

RELATED CASES

This is a continuation of Ser. No. 20,422 filed Mar. 17, 1970, now abandoned.

FIELD OF THE INVENTION

This invention relates to a new solid catalyst composition suitable for the hydroformylation, including hydroxyhydroformylation, of low molecular weight olefins to form the corresponding aldehydes and alcohols.

DESCRIPTION OF THE PRIOR ART

Processes directed to the production of reaction mixtures comprising substantial amounts of aldehydes and at times lesser amounts of alcohols by the reaction of olefinic compounds with carbon monoxide and hydrogen at elevated temperatures and pressures in the presence of certain catalysts are well known in the art. The aldehydes and alcohols produced generally correspond to the compounds obtained by the addition of a carbonyl or carbinol group to an olefinically-unsaturated carbon atom in the starting material with simultaneous saturation of the olefin bond. Isomerization of the olefin bond may take place to varying degrees under certain conditions with the consequent variation in the products obtained. These processes known in the industry, and referred to herein as hydroformylation, involve reactions which may be shown in the general case by the following equation:

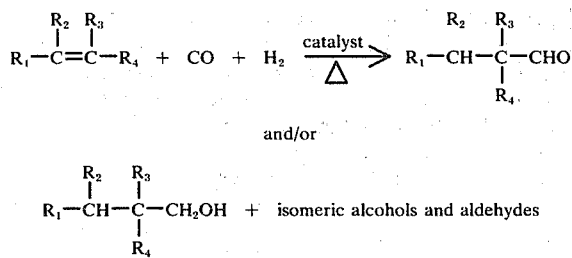

and/or $$R_1-CH-\underset{\underset{R_4}{|}}{\overset{\overset{R_3}{|}}{C}}-CH_2OH \;+\; \text{isomeric alcohols and aldehydes}$$

with $R_2$ on the CH.

In the above equation, each R represents an organic radical, for example hydrocarbyl, or a suitable atom such as hydrogen or a halogen. The above reaction is similarly applied to an olefinic linkage in a cycloaliphatic ring.

In the past, di(cobalt or nickel)octacarbonyls as such or in several different forms generally have been used as the catalyst for the hydroformylation of olefins. These catalysts which can be prepared from many forms of the metal, usually decompose rapidly unless high pressures (1000–4500 p.s.i.g.) of carbon monoxide are maintained. Correspondingly high pressures of hydrogen are also necessary. A most serious disadvantage of prior hydroformylation processes, however, has been the necessity of proceeding in two steps when alcohols are the desired product. Thus, in processes disclosed heretofore, it is generally necessary first to react the olefin to be hydroformylated with carbon monoxide and hydrogen to form the corresponding aldehyde. It is then necessary to carry out a second reaction with hydrogen to reduce the aldehyde to the alcohol in a separate operation. A different catalyst for the hydrogenation is usually needed for this second step since the hydroformylation catalysts heretofore employed are not sufficiently effective for this purpose. This results in the need for relatively expensive high-pressure equipment and for a large amount of such equipment to handle the two steps.

A further disadvantage inherent in processes directed to hydroformylation disclosed heretofore is a relative inability to direct the reactions involved to the production of predominantly terminal alcohols when the olefin contains more than two carbon atoms, particularly when the charge to the process comprises primarily internal olefins.

U.S. Pat. No. 3,239,569 to Slaugh et al., issued Mar. 8, 1966, discloses a homogeneous cobalt catalyst for use in the hydroformylation of olefins. The catalyst consists of a complex of cobalt with carbon monoxide and a trialkyl phosphine ligand. While the catalyst of that patent offers advantages over other prior art catalytic systems, the homogeneous system disclosed therein still does not offer the activity, stability and long-life requirements of commercial processing.

SUMMARY OF THE INVENTION

It is an object of this invention, therefore, to provide a novel catalyst system for the hydroformylation, including hydroxyhydroformylation, of olefins. More specifically, it is an object of this invention to provide a novel, heterogeneous, solid phase catalytic system for the hydroformylation of low molecular weight olefins to form the corresponding alcohols and aldehydes. A solid phase catalyst is highly desirable for a number of reasons, including the ease of handling of solids as contrasted with liquids. In addition, a solid catalyst can be more readily and completely separated from the low molecular weight alcohols and aldehydes produced by the hydroformylation. When surface phenomena are considered, a solid phase catalyst might also be more active and more selective than the homogeneous solution type of the same general ingredients. Despite these and other possible advantages, no significant solid phase catalyst of this type has been provided by the prior art.

It has been found in the present invention that complexes of one or both of cobalt and nickel with an electron donor ligand of organic-substituted elements of Group VA of the periodic table, said elements having an atomic weight of 15 to 83, on a solid, acidic, silica-based support, provide a solid phase composition having highly desirable physical and chemical characteristics and, when hydrocarbonylated, particularly excellent catalytic activity and selectivity for the hydroformylation, including hydroxyhydroformylation, of low molecular weight olefins. To obtain such solids the catalyst-forming reactants can be combined in a molar ratio of electron donor ligand to cobalt or nickel of about 1 to 4:1, preferably about 1.5 to 3:1, although either the metal or the ligand, preferably the ligand, can be present in excess. The complex, cobalt or nickel and electron donor ligand are present on the support in minor, catalytically effective amounts while the support is the major part of the catalyst. The metal and silica-based support can be present in amounts sufficient to yield an amount of cobalt or nickel, based on the support, of about 0.01 to 1 or more weight percent, preferably 0.05 to 0.6 weight percent.

In the preparation of the catalyst composition of the present invention, the cobalt or nickel source is provided by compounds of the metal which are at least slightly soluble in some solvent wherein the metal-Group VA ligand complex can be formed. Preferred are the weak field complexes, the ligands of which readily serve in solution as transfer agents. Suitable sources of the metal can include, for example, halides, e.g., $MCl_n$, $MBr_n$, $MI_n$, where M is cobalt or nickel and n (here and below) is the available valence of the metal; dihydrocarbyloxy cobalt, i.e., $M(OR)_n$, where R represents alkyl, aryl, aralkyl, and other hydrocarbon groups; dihydrocarbyloxy metal carboxylate, i.e., $(RO)_nMOOCR'$ where R and R' are as defined above as R; diphosphine complexes, e.g. $(M[(C_6H_5)_2PC_2H_4P(C_6H_5)_2]X_2$, where X is a halide. Also available as metal sources are chelates formed by the metal and weak field ligands, such as $\beta$-diketones or $\beta$-keto-carboxylic acid esters and salts of carboxylic acids. Examples of these types of metal sources include $\beta$-diketonato cobalt or nickel (II), acetylacetonato cobalt (II), propylacetonato cobalt (II), benzoylacetonato cobalt; chelates from $\beta$-ketocarboxylic acids esters; salts of saturated monocarboxylic acids, e.g. cobalt or nickel formate, cobalt propionate, cobalt caproate, cobalt octoate, cobalt palmitate, cobalt stearate, cobalt phenylacetate, cobalt phenylpropionate, and the like; salts of corresponding unsaturated monocarboxylic acids, e.g. cobalt or nickel acrylate, cobalt vinyl acetate, and the like; salts of unsaturated dicarboxylic acids, e.g. cobalt or nickel adipate, cobalt decane-1,10-dicarboxylate, and the like; salts of corresponding unsaturated dicarboxylic acids, e.g., cobalt or nickel muconate and the like; salts of cyclic and aromatic carboxylic acids, e.g., cobalt or nickel cyclohexane carboxylate, cobalt benzoate, cobalt phthalates, and the like; and alkoxycarboxylates, e.g., cobalt or nickel dimethoxyacetate and the like. Preferred as the source of cobalt or nickel is the cobalt or nickel acetylacetonate.

The electron donor ligand component employed in preparing the metal complex component of the catalyst of the present invention is preferably a triorganophosphine corresponding to the general formula $R_3P$ wherein R is a hydrocarbon radical, e.g. alkyl, aryl, alkaryl, aralkyl and cycloalkyl, of from 1 to about 20 carbon atoms, preferably 2 to about 6 carbon atoms and devoid of olefinic or acetylenic unsaturation; different R groups may, of course, be present in the same phosphine molecule. There is a strong preference for R being alkyl, e.g. lower alkyl. When the phosphine component contains aromatic groups it is generally preferred that these have mono-cyclic structures, e.g., that the groups be selected from phenyl, alkylphenyl, or phenylalkyl radicals.

Multifunctional phosphines of the formula $R_2$—P—P—$R_2$ such as bis(diphenylphosphine)ethane, may be used in place of the foregoing described unidentate phosphines. Phosphines may also be replaced by other electron donor ligands such as, for example, alkyl, aryl, alkaryl, aralkyl, or cycloalkyl phosphites, arsines, stilbines or bismuthines. Other monodentate or bidentate ligands containing nitrogen donating centers such as pyridine or alpha, alpha-bipyridyl, may also be utilized. It is, however, preferred that triorganophosphines be utilized. Examples of suitable phosphines for the composition of the present invention are triphenylphosphine, trimethylphosphine, tricyclohexylphosphine, tri-n-hexylphosphine, tri-n-decylphosphine, tribenzylphosphine, tri(4-n-butylphenyl) phosphine, and the like. Generally speaking, the electron donor ligand compounds of Group VA elements of the periodic table, having atomic numbers of 15 to 83 can be used in the catalysts.

The solid support of the catalyst of the present invention can be an acidic, silica-based material, e.g., having a D + L activity of at least about 20, preferably at least about 30 when determined according to the method of Birkhimer et al., "A Bench Scale Test Method for Evaluating Cracking Catalysts", Proceedings of the American Petroleum Institute, Division of Refining, Vol. 27 (III), page 90 (1947), and hereinafter referred to as Cat. A. The silica-based support preferably has a substantial surface area as determined by the BET nitrogen absorption procedure (JACS, Vol. 60, pp. 309 et seq.) (1938). The surface area of the support can be at least about 50 square meters per gram, and such surface areas are often up to about 500 or more m²/gm., preferably about 150 to 400 m²/gm. It is preferred that the catalyst support be relatively dry to avoid undue reaction with and loss of catalytic promoting materials. Thus, it is advantageous that the support be calcined, e.g., at temperatures of about 600° to 1500° F., or more, to reduce the water content, but such calcination should not be so severe that the support is no longer catalytically-active.

The support component contains other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of, or even to a major extent of, silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as a crystalline aluminosilicate, for instance, having pore openings in the 6 to 15 Angstrom unit range. The support often contains silica and alumina and such supports, whether naturally-occurring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystallite size as determined by half-width measurements of the (0, 4, 1) X-ray diffraction line calculated by the Debye-Scherrer equation. The mixture of the catalyst precursor components can be dried, e.g., at about 220° to 500° F. to convert the silica-alumina hydrogel to xerogel form. The dried material can then be calcined, e.g., at a temperature of about 700° to 1500° F., preferably about 800° to 1400° F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components is in the mixture in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about one sixty-fourth to one-half inch or more in diameter and about one thirty-second to 1 inch or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively. If present, the crystalline aluminosilicate is usually at least about 1 weight percent, preferably at least about 5 weight percent, based on the dried support. The alumina content from the silica-alumina xerogel and the separate alumina phase can be about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be a silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogel can be prepared by co-precipitation or sequential precipitation by either component being the initial material with at least the principal part of the silica or alumina being made in the presence of the other. Generally, the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above, the alumina hydrogel can be in the form of amorphous hydrous alumina or alumina monohydrate, e.g., of up to about 50A crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, one may separately filter the silica-alumina hydrogel and the hydrous alumina and intimately mix these materials, for instance, by colloidal milling. Although in this particular procedure a low sodium crystalline aluminosilicate can be added after the milling, this ingredient can also be combined before the colloidal milling operation. The mixture is dried, water-washed to acceptable concentrations of, for instance, sodium and redried in the preferred procedure. The drying, especially the initial drying, is advantageously effected by spray drying to give microspheres.

The crystalline aluminosilicate which can be present in the silica-based catalyst support of the present invention, can have pore openings of 6 to 15 A in diameter, and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-a and rare earth metals as cerium, etc. The metals may be present along with the ammonium or hydrogen cations.

The support can also be a naturally-occurring silica-based clay-type mineral, such as kaolin, which contains a major amount of silica and a minor amount of alumina, along with small amounts of other materials, such as sodium oxide, calcium oxide, magnesium oxide, iron oxide, potassium oxide, etc. A typical kaolin clay, after washing and calcining to remove water and other volatile materials which can amount to from about 10 to 20 weight percent of the uncalcined material, can contain from about 50 to 60 weight percent $SiO_2$, about 40 to 50 weight percent $Al_2O_3$, less than about 2 weight percent $Na_2O$ and less than about 1 weight percent of each of CaO, MgO and other metallic oxide impurities. The clay-type support can be fabricated into macrosize form, if desired, of a size of about one sixty-fourth to one-half inch or more in diameter and about one thirty-second to 1 inch or more in length.

The preparation of the overall catalyst composition is preferably conducted by first forming the complex of the electron donor ligand and the cobalt or nickel source. For illustration purposes, formation of the overall catalyst composition will be described in terms of cobalt, although it is understood that the nickel catalyst composition can be formed in the same manner.

The cobalt source and ligand can be present in about the stoichiometric amounts necessary to form the complex or more component can be present in an excess amount of that necessary for the formation of the complex.

Formation of the ligand-cobalt complex may be effected by simply mixing the two reactants in the presence of a suitable solvent for the complexing reaction. The mixing may be done at room temperature or up to about 300° F. The complex usually forms within about 20 to 40 minutes after mixing at elevated temperature. Suitable solvents for the complex-forming reaction include the same solvents which are suitable for use in the final catalyst composition. If desired, however, the complexing may be accomplished in a solvent which is unsuitable for use in the final composition; in this case the resultant complex can first be isolated from the reaction mixture and redissolved, or resuspended, in a proper solvent which is inert to the final catalyst composition.

Thus, for example, one method of preparing a phosphine cobalt complex can involve stirring, preferably at room temperature, a mixture of tri-n-butylphosphine, cobalt acetylacetonate and chlorobenzene. In another method, the complex may be prepared by refluxing an alcohol, e.g. ethanol, solution of the phosphine, say tri-n-butylphosphine, and cobalt acetylacetonate, preferably at a temperature of about 150° to 250° F., and isolating the resultant complex from the reactant mixture. This approach is often preferred where the metal reagent contains some water of hydration, as the water will be removed from the complex when the latter is separated from the alcohol solvent.

In either case, the cobalt-triorgano phosphine complex can be dissolved in a suitable solvent, e.g., ethanol, methanol, benzene, chlorobenzene, or the like, and charged to a reactor. Hydrogen and carbon monoxide gas can then be introduced separately, or as a premixed gas, in a molar ratio of hydrogen to carbon monoxide of from about 1:1 to 5:1, preferably from about 1.2:1 to 3.5:1, at a temperature of from about 60° to 400° C., preferably from about 150° to 250° C., and a pressure of from about 500 to 3000 psig., preferably from about 700 to 1500 psig. to obtain the hydrido-cobalt carbonyl-triorgano phosphine complex. The solid support, in finely-divided form, is combined with the complex in the solvent and the system is agitated for a time sufficient to affix the complex on the support.

The solid supported catalyst can also be prepared in situ by charging the metal source, such as cobalt acetylacetonate, the electron donor ligand, such as tributyl phosphine or triphenyl phosphine, and the support in finely-divided form in a suitable solvent to an autoclave reactor and allowing these components to react under a premixed gas of hydrogen and carbon monoxide of a molar ratio of hydrogen to carbon monoxide of from about 1:1 to 5:1 at a pressure of from about 1000 to 18000 psig., and a temperature of from about 150° to 195° C. for about 1 hour. The resulting supported catalyst system can be separated by removing the liquid phase from the reactor. If desired, the low molecular weight olefin can be charged to the catalyst system before separation and the hydroformylation reaction carried out in the presence of the solvent. After the reaction is completed, the liquid reaction mixture can be separated and removed from the reactor. Alternatively, the catalyst components, support and low molecular weight olefin can be charged simultaneously in a solvent to the autoclave under conditions as set forth above, thus allowing the system to simultaneously undergo formation of the solid supported catalyst system and the hydroformylation of the low molecular weight olefin.

The solid supported catalyst system can also be prepared by dissolving the metal source such as cobalt naphthenate or cobalt acetylacetonate in a solvent such as benzene or alcohol. The solid support is added to the resulting pink solution and the system is agitated at room temperature overnight yielding a colorless supernatant liquid and pinkish-colored support particles. These cobalt-impregnated support particles are then filtered, washed and dried in an oven. The dried cobalt-impregnated particles are charged to a reactor along with an electron donor ligand, such as tributyl phosphine, in a solvent. The system is pressured with hydrogen and carbon monoxide under conditions as set forth above for in situ preparation and the hydrido-cobalt carbonyl-triorgano phosphine complex on a solid, acidic, silica-based support catalyst recovered. An olefin feed can be introduced with the hydrogen and carbon monoxide also in the manner set forth above for in situ preparation.

The supported catalyst composition of the present invention is effective for hydroformylation, including hydroxyhydroformylation, of olefinic hydrocarbons, e.g., of 2 to about 16 carbon atoms, preferably 3 to 10 carbon atoms, and is highly desirable for such uses. For example, it is possible to provide alcohols, aldehydes, and the like fromm aliphatic mono-olefins. Of particular interest, however, is the selective activity of the present catalyst composition in the hydroformylation of pentene to form hexanol and hexanal. The selectivity of the catalyst of the present invention is exceptional for this type of reaction, while the activity is high as well, resulting in greater efficiency in producing such alcohols and aldehydes. In the prior art, such alcohols are produced in rather minor amounts. With the present catalyst, it is possible to obtain such alcohols, e.g., n-hexanol and isohexanol as the major product.

Hydroformylation can generally be effected by contacting the olefinically-unsaturated feed with hydrogen and carbon monoxide under pressure and in the presence of the catalyst at a temperature of about 100° to 350° C., preferably about 150° to 200° or 250° C. Elevated temperatures ordinarily can be maintained by the heat of reaction without external heating means. In many cases, it may be necessary to control the temperature by cooling, as for example, by circulating a cooling medium through heat exchange tubes in the reactor. Pressures of up to about 2500 or more psig, preferably about 500 to 2000 psig, are suitable with the catalyst composition of the present invention. The amount of catalyst composition used in the reaction is that sufficient to effect hydroformylation or hydroxyhydroformylation of the feed and often the olefin feed contacts the catalyst at the rate of about 1 to 20, preferably 1 to 10, WHSV (weight of olefin per weight of catalyst per hour). The process is applicable to continuous processing, e.g., with a catalyst slurry or a fixed bed, as well as batch processes. The hydrogen and carbon monoxide are preferably introduced into the reactor as a premixed gas containing a molar ratio of hydrogen to carbon monoxide from about 1.1:1 to 5:1, preferably from about 1.2:1 to 3.5:1. The catalyst system of the instant invention can be readily regenerated by the addition of fresh Group VA electron donor ligands to the deactivated catalyst.

DESCRIPTION OF SOME PREFERRED EMBODIMENTS

The preparation of an acidic silica-alumina support of this invention is illustrated by Examples I–III, and the support contains a separate phase of alumina.

EXAMPLE I

An alumina hydrogel is prepared as follows:

In a tank containing 5700 gallons of water at 85° F., are dissolved 300 lbs. of soda ash. When the soda ash has been dissolved, 180 gallons of a 39% concentration aqueous sodium aluminate solution are pumped into the tank in about a 15-minute period. The contents of the tank are at about 84° F. Six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution which, while being added, is also diluted continuously with water at a rate of 35 gallons per minute over a 7½ minute addition period. The contents of the tank are heated to about 100° F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90° F., and 865 gallons of sodium silicate solution (28.8 weight percent $SiO_2$, 40–41.5 Baume at 68° F., and $Na_2O:SiO_2$ ratio of 1:3.2) is added. The batch is stirred for five minutes. The concentration of the sodium silicate, as $SiO_2$, in the batch is 6.3 weight percent.

With the batch at 90° F., 302 gallons of 34.5 weight percent sulfuric acid solution at 182° F. are added over a period of 45 minutes. The gel forms about 35 minutes after acid addition is begun. Then the pH is adjusted to 8.0–8.5. The batch is agitated for 10 minutes.

Then 715 gallons of alum (7.8 weight percent, as $Al_2O_3$) is added to the gel over a period of about 36 minutes. The batch is agitated for an additional 5 minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for 1 hour. The finished batch has a pH of 5.5 to 5.6 and a temperature of about 110° F. The aqueous gel mixture is then pumped to a dewatering filter and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propellor, for about 10 minutes to give a thorough dispersion. The product was stirred one minute at 14,500 rpm, in a Waring Blender and dried in a laboratory spray-drier. The spray-dried material was washed with water to acceptable impurity levels and dried at 230° F. The washed and dried material analyzed 0.08% $SO_4$ and less than 25 ppm $Na_2O$. The dried material as such was used as the catalyst support, as were extruded forms thereof and tablets (pellets) having diameters of about one-eighth inch and lengths of about one-eighth to one-half inch. Before use, the catalyst support was calcined in a muffle furnace by raising the temperature by 300° F. per hour until 1350° F. was reached. This temperature was then held for three hours. The calcined particles had a surface area of about 320 to 340 square meters per gram.

EXAMPLE IV

A 300 cc. stainless steel autoclave, provided with a magnetic stirrer, was used as a reactor, and was connected to a source of a premixed hydrogen-carbon monoxide. Propylene, taken as a typical olefin, was hydro- and hydroxy-formylated by reaction with carbon monoxide and hydrogen with a hydrido-cobalt-carbonyl-tri-n-butylphosphine ($Bu_3P$) complex on the support. The supported catalyst was prepared in situ by mixing cobalt naphthenate, tri-n-butylphosphine and microspheroids of Example III and having the following particle size distribution:

| | |
|---|---|
| 0 – 10μ | 0.0 wt. % |
| 10 – 20 | 0.5 |
| 20 – 40 | 20.3 |
| 40 – 80 | 67.4 |
| >80 | 12.3 | in the presence of solvent and heating in an atmosphere of carbon monoxide and hydrogen to about 140°–160° C., thereby forming the solid cobalt-carbonyl-tri-n-butylphosphine catalyst. A series of batch runs was intermittently made with this solid catalyst over a prolonged period.

In the first run, 1.83 m (milli) moles Co-naphthenate (10.5% Co), 40 ml o-xylene and 10.0 g microspheroids were charged to the reactor, and the reactor was agitated under an atmosphere containing carbon monoxide and hydrogen in a molar ratio of 1:1 (1400 psig) at 140°–150° C. for about 30 minutes. The system was allowed to cool and settle overnight. The gas phase was slowly drained from the reactor, and then 6.0 m moles of tri-n-butylphosphine and 10.0 g of propylene added to the reactor. The pressure of the reactor was 150 psig at this stage, and was pressured to 550 psig with a premixed gas, 1:1 H$_2$:CO, and then to 750 psig with H$_2$. The reactor was tightly closed and heating was started using an external heater. The temperature of the reactor increased from 31° to 158° C. over about an hour period, and consequently, the initial pressure of the system was raised to 1380 psig. The initial pressure drop was noticed under 1380 psig at 150° C. The reaction was allowed to proceed by agitating the system vigorously at the temperature range of 50°–174° C. for an hour period. The pressure of the reactor dropped from 1380 psig to 800 psig within 23 minutes. At this stage, the reactor was open to a cylinder, which contained a premixed gas (1:1 molar ratio of H$_2$/CO) at 860 psig. The mixed gas was continuously supplied to the reactor under a constant pressure (860 psig). The reactor was kept at 174°–172° C. for an additional 37 minutes. No significant pressure drop was observed during a last 10–15 minute period. The reaction was quenched using an internal cooling coil and allowed to settle at 20° C. for 1½ hours. A red-brown reaction mixture was discharged from the reactor through a filter attached to the bottom of the autoclave. The color of the reaction mixture indicated that the amount of the solid support charged in the reactor was not sufficient to support all the catalytic species formed in the system. Thus, some portion of the catalytic species was fixed on the solid, and the remainder of the catalyst was discharged with the reaction mixture. Due to the characteristic nature of the support to absorb some liquid into its microspheroid structure and to the construction of the autoclave reactor, quantitative removal of the reaction mixture from the reactor was impossible, and thus some contamination from preceding runs was unavoidable throughout consecutive runs. The product was analyzed by means of a gas chromatographic technique. A minimum conversion of the propylene was estimated to be 51%. The product distribution was 9.8% isobutanal, 36.4% n-butanal, 10.1% isobutanol, 30.3% n-butanol, and 13.4% unidentified products. The solid catalyst left inside of the autoclave was washed twice with fresh portions of o-xylene. In the second run, exactly the same reaction was repeated as described in the first run.

The initial pressure drop was observed at 174° C. and 1290 psig after about an hour induction period. The reaction was allowed to proceed at 179°–162° C. for 50 minutes. During this period, the pressure of the reactor dropped from 1290 psig to 800 psig. The reactor was then connected to a cylinder, which supplied a premixed gas (H$_2$:CO(1:1)) under 860 psig. The system was kept at 100° C. for an additional 10 minutes, and a very light orange-colored reaction mixture was removed from the reactor. The third run was immediately started by feeding 10 g. propylene with 40 ml p-dioxane solvent. The reactor was pressured with a premixed gas (1:1 H$_2$/CO) from 300 psig to 700 psig, and then hydrogen was introduced to raise the pressure to 900 psig at 89° C. After about an hour induction period, the reactor was kept at 175°–180° C. for 50 minutes. The pressure of the reactor dropped from 1270 psig to 1055 psig. A light yellowish reaction mixture was removed from the reactor. In the fourth run, the same reaction was repeated with the 24 hour aged catalyst. The reactor was kept at 180°–185° C. for 50 minutes, and the pressure drop from 1750 psig to 1410 psig was observed during this period. A light yellowish reaction mixture was discharged from the reactor. This data clearly indicates that the catalytic activity of the solid catalyst was maintained very well throughout these runs. Actually, the catalytic activity of the catalyst based on conversion of propylene tends to increase from the second run to fourth run. Details of these results are listed in Tables I and II.

The fifth run was made with 25 g of pentene-1 in the absence of solvent. Although the analysis of the product was not completed, major components in the product were found to be hexanols.

EXAMPLE V

A homogeneous catalyst solution was prepared from 3.0 m moles cobalt acetylacetonate, and 6.0 m moles Bu$_3$P in 50 ml decanol. The reactor was purged with hydrogen, and 20 g of propylene was introduced to the reactor. The reactor was immediately pressured with a premixed gas (1:1 H$_2$:CO) to 1000 psig at 44° C. After an hour induction period, reaction was started under 1550 psig at 135° C. The system was allowed to react at 135°–150° C. for 1½ hours. During this period, the pressure of the system dropped from 1550 psig to 850 psig. A red-orange solution was discharged from the reactor, and analyzed by means of gas chromatographic techniques. The propylene feed was reacted in 28% conversion to give 11.3% isobutylaldehyde, 53.9% n-butylaldehyde, 0.4% isobutanol, 15.0% n-butanol, 2.3% 2-ethylhexanol, and 16.1% heavy products. The results obtained from this and previous runs indicate that the supported catalyst exhibits a higher (or at least equal) catalytic activity than that of the corresponding homogeneous system.

EXAMPLE VI

Cobalt acetylacetonate and n-Bu$_3$P in decanol were stirred for two days, more decanol was added and the mixture charged to an autoclave with the microspheroids of Example III added to the system. The catalyst system prepared in this manner was then used in the hydroformylation of propylene in a series of five runs extending a period of 97 hours. The catalyst left from the fifth run was taken out of the reactor, and exposed to air for about 5 weeks. The aged catalyst was recharged to the reactor with propylene and fresh Bu$_3$P under reaction conditions similar to those of the first five runs. The propylene feed was reacted in 43% conversion. This result clearly indicates that the aged catalyst can be successfully regenerated by adding a fresh portion of Bu$_3$P. The catalytic activity of the regenerated catalyst was raised to almost the same level as the virgin catalyst and it was also maintained in the next run (the eighth run). The entire sequence of runs was made over a 940 hour period.

EXAMPLE VII

Cobalt (III) acetylacetonate (4.0 m moles) was dissolved in 65 g decanol and the resulting solution was quantitatively transferred to a 300 cc autoclave with the aid of 20 g of an additional portion of decanol. The support of Example III in the form of microspheroids (50 g) was then introduced to the system. The reactor was pressured with a premixed gas (1:1, H$_2$:CO) in the absence of tri-n-butylphosphine ligands and reaction was run with 10 g propylene under 1750–1145 psig at 160°–185° C. for 4½ hours (after the 2 hour induction period). The propylene feed had reacted to a very limited extent (0.7% conversion) in this run. The catalyst left inside of the reactor from the first run was rinsed twice with decanol (90 ml), and employed for repetition of the same reaction in the second run. The catalyst still showed poor activity. In the third run, 3.0 m moles tri-n-butylphosphine in 10 ml decanol was introduced to the solid catalyst aged from the preceding two runs. The system was agitated at room temperature for an hour. Immediately after 10 g propylene was fed to the reactor, the reactor was pressured with a premixed gas (1:1, $H_2$:CO) and heating was started. After a two hour induction period, reaction was allowed to proceed under 1670–900 psig at 166°–172° C. for 3½ hours. A colorless reaction mixture with a small portion of gray catalyst debris was removed.

The fourth run was again made with the 74 hour aged catalyst in the absence of solvent. Propylene (10 g) was reacted at 156°–161° C. for 3½ hours. During this period the maximum pressure 1500 psig at 165° C. dropped to 800 psig. A clear reaction mixture was removed from the reactor. Conversions of the propylene feed in the third and fourth runs were 27% and 35% respectively. Details of these runs are tabulated in Table I and II. These results clearly demonstrate that the tri-n-butylphosphine increased the catalytic activity of the solid catalyst without $nBu_3P$ to a remarkable extent. A pink solid catalyst was obtained from these four consecutive runs. The resulting pink solid catalyst slowly turned purple when it was exposed to air.

EXAMPLE VIII

Co-naphthenate and microspheres of the support of Example III were added to benzene in an Erlenmeyer flask. These components were stirred overnight in a nitrogen atmosphere at room temperature. A pink solution of Co-naphthenate in benzene was gradually absorbed in the support and a clear colorless supernatant liquid was left over pink microspheres. The resulting Co-impregnated microspheres were filtered, and washed several times with fresh portions of benzene. The washed microspheres were dried in an oven for 24 hours. The microspheres impregnated with cobalt naphthenate were transferred to an autoclave, with $Bu_3P$ and decanol. Propylene was introduced to the system, and the reaction was run under conditions similar to Example VI. The propylene feed was reacted in 30% conversion in this run. The solid catalyst, left inside of autoclave from the first run, was washed three times with fresh portions of cyclohexane. The resulting solid catalyst was aged in the reactor for 22 hours. The second run was started by feeding propylene along with cyclohexane. Reaction conditions similar to the first run were employed. The conversion of the propylene feed was increased to 45% in this run. The results obtained from these two runs clearly indicate that the preimpregnated microspheres (with Co-naphthenate also gives a very active catalyst.

EXAMPLE IX

The same reaction (as the second run in Example IX) was carried out in the absence of a cobalt-complex. No significant reaction was noticed. The $Bu_3P$-solid, acidic, silica-based support system showed very limited activity for the hydroformylation of propylene in the absence of cobalt.

TABLE I

| Example No. | Run No. | Catalyst Composition | | | | | Reaction Condition | | | |
|---|---|---|---|---|---|---|---|---|---|---|
| | | Co mm | $R_3P$ m m | Support g | Solvent ml | Catalyst Aged hrs. | Temperature °C. | Pressure psig | $H_2$/CO | Reaction period hrs. |
| | | Co-Naph. | | | o-xylene | | | | | |
| | 1st | 1.83 | 6.0 | 10.0 | 40 | — | 150–174 | 1380–800 | 2 | 1 |
| | 2nd | <1.83 | <6.0 | 10.0 | 40 | 4 | 160–179 | 1290–800 | 2 | 1 |
| IV | 3rd | <1.83 | <6.0 | 10.0 | p-dioxane 40 | 6 | 170–180 | 1270–1055 | 2 | 5/6 |
| | 4th | <1.83 | <6.0 | 10.0 | 40 | 24 | 180–185 | 1750–1410 | 2 | 5/6 |
| | 5th | <1.83 | <6.0 | 10.0 | 0 | 27 | 178–187 | 1510–1250 | 1 | 3 |
| | 1st | 4.0 | 0 | 50.0 | 85 | — | 160–185 | 1750–1145 | 1 | 4½ |
| VII | 2nd | 4.0 | 0 | 50.0 | 25 | 26 | 160–172 | 1650–1300 | 1 | 4½ |
| | 3rd | 4.0 | 3.0 | 50.0 | 10 ml | 49 | 166–172 | 1670–900 | 1 | 3½ |
| | 4th | 4.0 | 3.0 | 50.0 | 0 ml | 74 | 156–161 | 1500–800 | 1 | 3½ |

TABLE II

| Example No. | Run No. | Feed, g | | Selectivity to Alc. and Ald., % | Feed Reacted m Mole | Conversion % | Product Distribution | | | | | | |
|---|---|---|---|---|---|---|---|---|---|---|---|---|---|
| | | | | | | | $iC_4$—Al | $nC_4$—Al | $iC_4$—OH | $nC_4$—OH | Unknown** | $2EtC_6$—OH | Heavy Product |
| | 1st | $C_3^=$ | 10 | 84 | 122 | 51 | 9.8 | 36.4 | 10.1 | 30.3 | 13.4 | — | — |
| | 2nd | " | 10 | 71 | 77 | 31 | 11.4 | 41.2 | 4.9 | 15.9 | 14.9 | — | 11.7 |
| IV | 3rd | " | 10 | 91 | 118 | 50 | 12.6 | 60.3 | 5.0 | 15.6 | 6.5 | — | — |
| | 4th | " | 10 | 90 | 188 | 79 | 21.9 | 53.7 | 4.8 | 12.3 | 7.3 | — | — |
| | 5th | $C_5=1$ | 25 | | | | | | | | | | |
| | 1st | $C_3^=$ | 10 | — | 17 | 0.7 | 1.6 | 7.0 | 6.3 | 9.7 | 25.1 | 2.8 | 47.5 |
| | 2nd | " | 10 | — | 19 | 0.8 | 1.6 | 9.8 | 5.8 | 11.5 | 25.1 | 2.8 | 43.8 |
| VII | 3rd | " | 10 | 56 | 64 | 27 | 1.6 | 2.6 | 15.0 | 25.7 | 5.8 | 10.0 | 39.8 |
| | 4th | | 10 | 36 | 83 | 35 | 2.1 | 2.0 | 15.1 | 23.7 | 4.5 | 4.0 | 48.6 |

**2Et—$C_6$—Al and 2Et-hexenal are included.

EXAMPLE X

A 300 cc autoclave, equipped with a magnetic stirrer, was used as a reactor, and was connected to sources of hydrogen, carbon monoxide and propylene. Propylene, taken as a typical olefin, was hydro- and hydroxyhydroformylated by reaction with carbon monoxide and hydrogen with a hydrido-cobalt-carbonylphosphine complex fixed on the support of Example III. The fixed solid catalyst was prepared in situ by mixing cobalt naphthenate, tri-n-butylphosphine, and microspheres (the support) in the presence of solvent and heating under an atmosphere of carbon monoxide and hydrogen with or without an olefin substrate, thereby forming the solid catalyst. A series of batch runs was intermittently made with this solid catalyst over a prolonged period.

In the first run, 1.6 mm cobalt naphthenate (10.5% Co, and 6.0 mm Bu$_3$P were charged to the autoclave along with 50 ml benzene under a carbon monoxide atmosphere. These were allowed to react under 1250–1200 psig (CO pressure) at 140°–145° C. for a 6-hour period. The reactor was allowed to cool and kept under 800 psig CO pressure at room temperature over a weekend (~ 65 hours). As soon as the pressure of the reactor was released, 10 g of the support microspheres was introduced to the reactor under hydrogen atmosphere. Propylene (18.0 g) was fed to the reactor, and the total amount of benzene in the reactor was adjusted to 65 ml. The reactor was pressured to 530 psig with hydrogen and then to 900 psig with carbon monoxide at 20° C. The reactor was heated by an external source for about 1½ hours. The temperature and pressure of the reactor were 147° C. and 1355 psig, and the initial pressure drop was observed at this stage. The reactor was further kept at 147°–170° C. for a 1½ hour period. The pressure dropped from 1355 psig to 700 psig during this reaction period. When the reaction was quenched by running cold water and the reactor allowed to cool to room temperature, a reddish-orange reaction mixture was discharged, and the solid catalyst left inside of the reactor was rinsed with a 30 ml portion of fresh benzene. Both the discharged reaction mixture and rinsed benzene solution were analyzed by means of gas chromatographic technique. About 31% of the feed was converted to give the following product distribution: 10.3% isobutanal, 46.9% n-butanal, 13.9% isobutanol, 11.3% n-butanol, 2.5% 2-ethylhexanal, 12.1% 2-ethyl-2-hexenal, and 3.4% unidentified products.

The exactly same batch reactions were consecutively repeated in the presence of benzene or p-dioxane as a solvent with the solid catalyst over a 57-hour period. Details of the results and reaction conditions are listed in Tables III and IV. These data clearly indicate that the catalytic activity of the solid catalyst, based on the conversion of propylene, was maintained at similar level throughout these runs, and that the product distribution remains essentially the same for the prolonged reaction period. The ratio of n-product (plus the products derived from n-isomers) to iso-product was maintained in the range of 75–86/1.

EXAMPLE XI

Both 1.4 mm cobalt naphthenate and 15 g of the microspheres of Example III were charged along with benzene in a 300 cc autoclave. The autoclave was closed tightly, and purged with hydrogen for a prolonged period before 3.0 mm tri-n-butylphosphine was injected into the system. As soon as the introduction of tri-n-butylphosphine was completed, the reactor was pressured to 1500 psig with carbon monoxide and hydrogen (H$_2$/CO = 1) at 100° F. The reactor was slowly heated to attain 141° C. in about 3 hours. The maximum pressure of the reactor, 1960 psig, at this stage dropped to 1010 psig by keeping the reactor at 141°–173° C. for 2⅔ hours. After the reaction was quenched by running cold water through an inside cooling coil, a light brown reaction mixture was discharged from the reactor. The solid catalyst left inside of the reactor was rinsed with 35 ml of benzene. Both the discharged reaction mixture and the rinsed solution were analyzed by means of gas chromatographic techniques. Two more batch runs were repeated under similar conditions with the same solid catalyst over a 145 hour period. The results obtained from these runs are summarized in Tables III and IV.

The fourth run was made in the presence of tributylamine (25 ml) with the catalyst aged for 149 hours from the three preceding runs. After the reaction was allowed to take place under 1980–800 psig (H$_2$/CO = 1) at 151°–173° C. for 1½ hours, a red reaction mixture was removed through the filter attached on the bottom of the autoclave, and the solid catalyst was washed twice with two fresh portions of benzene. These were also analyzed by means of gas chromatographic techniques. Data obtained from the analysis of the washing solution indicated that a significant amount of the product was retained even in the second washing solution. Due to the characteristic nature of the solid catalyst to retain some liquid into its microspheroid structure from the reaction system, quantitative determination of the product was impossible throughout the consecutive batch runs unless the reactor can be continuously operated.

Judging from the data listed in Tables III and IV, the presence of tri-n-butylamine remarkably increased the conversion of the propylene from 11–22% to 32% and at the same time, enhanced the ratio of n-products/iso-products from 71–81/1 to 85/1. The dimer products derived from the aldol condensation of n-butanal was also substantially increased with the aid of tri-n-butylamine.

In the fifth run, the effect of potassium hydroxide on the solid catalyst system was examined. After a hexanol solution of potassium hydroxide (1 g KOH in 70 ml hexanol) was injected to the solid catalyst, which had aged for 168 hours, from the preceding runs, 20 g of propylene was fed and was pressured to 1350 psig at 78° F. (H$_2$/CO = 1.2). An initial pressure drop was noticed after the reactor was slowly heated for 1½ hours. When the reactor was quenched, the catalyst was still active because the pressure drop of the system was persistently observed. A light-brown mixture removed from the reactor was analyzed by means of gas chromatographic techniques. About 60% of the propylene feed (20.0 g) was converted to give 7.4% isobutanal, 20.7% n-butanal, 3.0% isobutanol, 7.2% n-butanol, 8.0% 2-ethylhexanal, 26.8% 2-ethyl-2-hexenal, 4.3% 2-ethylhexanol, and 22.7% unidentified products. The addition of KOH dissolved in n-hexanol remarkably enhanced the conversion and the dimeric products. It seems that potassium hydroxide does not poison the solid catalyst under the reaction conditions employed in this run.

The sixth run as made in the presence of triethylamine with the solid catalyst aged for 173 hours from the preceding runs. Both propylene (20 g) and triethylamine (15 ml) were charged along with 55 ml benzene to the reactor. The reactor was kept under 2110-1900 psig (H$_2$/CO = 1) at 260°–346° F. for 1½ hours. No significant reaction had taken place. It is quite obvious that triethylamine is a principal source for deactivation of the catalyst system. It could be attributed to the strong coordinating tendency of triethylamine to cobalt in the catalyst. The grey solid catalyst, which was thoroughly rinsed and dried, was analyzed, for cobalt and phosphorus. It retained about 0.5 mm cobalt and 0.3 mm phosphorus on the support solid phase. Based on the data listed in Tables III and IV, it is reasonable to think that the leaching of cobalt from the solid phase has taken place, in most part, in the last run.

EXAMPLE XII

A phosphine complex, $[Co(CO)_3(Bu_3P)]_2$, which was prepared by reacting $Co(CO_3)_2$ and $Bu_3P$ in pentane under high pressure of mixed gas of $H_2$ and CO and was used for the present work. Microspheres of the support of Example III (15g) was charged along with benzene in a 300 cc autoclave. After the system was thoroughly purged with hydrogen for 2/3 hours, a complex solution (1.7 mm $[Co(CO)_3(Bu_3P)]_2$ dissolved in benzene) was injected through a serum cap. As soon as 20 g propylene was fed into the reactor, the reactor was pressured with $H_2$ and CO ($H_2/CO = 1$) to 1400 psig at 70° F. The reactor was slowly heated to attain 1700 psig at 225° F. within 40 minutes. The initial pressure drop was noticed at this stage, and the pressure continuously dropped to 1340 psig for about 30 minutes (at 225°–283° F). After this stage, the pressure drop was virtually stopped for 20 minutes. The system was again pressured with hydrogen to 1820 psig, and the system was held to 1820–1830 psig at 300°–345° F. for about 20 minutes without observing any significant pressure drop. A very slow second pressure drop was noticed under 1830 psig at 145° F., and the pressure drop continued for an additional 1⅓ hours. The pressure dropped slowly (but persistently) during this period to give 1600 psig when the reaction was quenched by running cold water through a cooling coil. A yellow-brown reaction mixture was discharged from the reactor and the second run was immediately followed by feeding 20 g propylene to a mixture of 15 ml $Bu_3N$ and 55 ml benzene. The reactor was pressurized from 120 psig to 750 psig with carbon monoxide and then to 1450 psig with hydrogen at 90° F. The system was heated slowly to attain 2120 psig at 330° F. within an 1½ hour period. The initial pressure drop was observed at this stage, and the maximum pressure, 2120 psig, dropped to 1150 psig in 50 minutes. The system was again pressured to 1600 psig at 357° F. with hydrogen. The reaction as allowed to proceed for an additional 20-minute period. During this period, the pressure dropped to 1150 psig. The reaction was quenched, and a red reaction mixture was discharged from the reactor. The solid catalyst left inside of the autoclave was rinsed with 60 ml benzene. Both the discharged reaction mixture and the rinsed solution were analyzed by means of gas chromatographic techniques. About 43% of the propylene feed was converted to give 9.1% isobutanal, 41.7% n-butanal, 3.6% iso-butanol, 13.3% n-butanol, 7.9% 2-ethylhexanal, 21.0% 2-ethyl-2-hexenal and 3.3% unidentified products. The weight ratio of n-products (plus the products derived from n-butanal) to iso-products was found to be 7/1. The results obtained fron these runs clearly indicate that the initial phase of activity observed in this work exhibited at somewhat lower temperature (~115° C.) than the homogeneous system without the support. It is also indicated that the catalyst deactivated by either a prolonged continuous run or poisoning effect of oxygen can be effectively regenerated by injecting fresh tri-n-butylphosphine (or tri-n-butylamine) to the inactivated catalyst. A large excess of phosphine remarkably increases the level of the catalytic activity of the active catalyst, while in a homogeneous system, a large excess of phosphine ligand tends to exhibit a retarding effect on the catalytic reaction. It further appears that the solid catalyst is not merely a soluble homogeneous catalyst species impregnated on the support base. In short, the catalytic composition of the solid catalyst and homogeneous catalyst are believed to be different. It appears that there is no definite advantage to prepare the solid catalyst from the cobalt complex, $Co_2(CO)_6(Bu_3P)_2$. The solid catalyst can be readily prepared in situ from a cobalt salt.

In one phase of this work, the effect of air on the catalytic reaction as studied. The catalyst system made as above in benzene in an autoclave was exposed to the air for one-half hour. The autoclave was then sealed and propylene was reacted in the presence of air and reaction conditions similar to those above, including the addition of a small amount of fresh $Bu_3P$ injected to the system. A qualitative gas chromatographic analysis indicated that the conversion of the propylene feed to aldehydes and alcohols (including dimeric aldehydes and alcohols) was substantial. This demonstrates that the solid catalyst exposed to air was successfully activated by the addition of fresh $Bu_3P$.

EXAMPLE XIII

A solid catalyst was prepared from $[Co(CO)_3(Bu_3P)]_2$, $Bu_3P$, and the support of Example III in benzene under a premixed gas in the manner of the previous Example XII. Excess $Bu_3P$ was injected at the beginning of the reaction. Actual conversion of the feed in this run was estimated to be in the range of 80–85%.

Two more batch runs were consecutively made with the solid catalyst over a 25-hour period. The catalytic activity based on the apparent conversion of the propylene feed was kept at a high level. These results clearly demonstrate that the presence of excess phosphine ligand enhance the catalytic activity of the catalyst consisting of $[Co(CO)_3(Bu_3P)]_2$ and the support of this invention.

EXAMPLE XIV

The support of Example III was introduced to a pale yellow solution of bis(triphenyl phopshine)nickel carbonyl in a toluene solvent. After a period of time sufficient for impregnation, the light brown-colored pellets were removed and transferred to a reactor. Pentene-1 was reacted in the presence of a mixed gas of $H_2$ and CO under reaction conditions similar to those of Example XII. About 73% of the feed was converted with the $C_6$ aldehyde being a principal product of the reaction. It is thus shown that the solid catalyst system including nickel is an effective hydroformylation catalyst.

EXAMPLE XV

Interaction of n-butanal or iso-butanal with the base was investigated at room temperature, since the base was found to play a promoting effect for the aldol condensation of aldehydes obtained from the hydroformylation of propylene in the preceding examples. Both 100 ml of n-butanal and 20 g microspheres of the support of Example III were charged to a magnetically stirred flask. The system was vigorously stirred at room temperature for about 3 hours. The liquid phase became more viscous indicating that some polymerization was taking place. After unreacted butanal was removed from the filtered liquid portion by vacuum distillation, the residue was analyzed by IR, NMR and mass spectroscopic techniques to be mainly tri-n-propyltrioxane.

Similar results were also obtained with silica gel, Nalco low alumina, and silica-alumina.

As the second phase of this work, 100 ml of isobutanal was treated in the same fashion with the microspheres. After a 72-hour period of agitation at room temperature, the system was solidified with white needle-like crystals. When the unreacted isobutanal was removed under a high vacuum, the resulted crystalline product was analyzed by means of IR, NMR and mass spectroscopic technique and was identified as triiso proyltrioxane.

Of course, under the oxo reaction conditions no cyclotrimerization of aldehyde product can be expected. Instead, aldol condensation was promoted by the presence of the support of this invention. Colorless aldehydes turned to a red-brown solution in the course of this work.

EXAMPLE XVI

Triphenylphosphine was investigated in this run. About 1.1 mm cobalt naphthenate (10.5% Co) and 3.5 mm triphenylphosphine were charged along with 75 ml benzene in a 300 cc autoclave. These two components were allowed to react at 80° C. under a nitrogen atmosphere overnight (~14 hours) and the temperature of the reactor was slowly raised to 120° C. for an hour period. The system was cooled and 15 g microspheres of the support of Example III was added to the system. Propylene (23 g) was allowed to react under 1485–1400 psig at 160°–183° C. for 3½ hours. A very slow pressure drop was noticed during this period and a yellow reaction mixture was removed from the reactor. Only 3.4% of the feed was converted. The same reaction was reported in the second run with the solid catalyst aged for 47 hours. A very limited catalytic activity was also exhibited in this run.

EXAMPLE XVII

To study the effect of the support of this invention on the catalytic reaction, the amount of the support was reduced to 5 g on this experiment. To a 300 cc autoclave free from any metallic contamination, both 5 g of the amount of the support and 80 ml benzene were charged and the complex solution(0.691 g [Co(CO)$_3$.(Bu$_3$P)]$_2$ in 20 ml benzene) was added to the system after the reactor was flushed with nitrogen. The propylene feed (20.3 g) was allowed to react under 1750–1000 psig (H$_2$/CO = 1.1) and 135°–160° C. for an hour. Only 10% of the feed was reacted. It is quite obvious that reduction of the support from 15 g to 5 g in the catalyst system is responsible for the decrease of the activity. The ratio of cobalt to support affects the nature of the catalytic reaction. The cobalt should preferably be present in the catalyst in an amount of about 0.05 to 0.6 weight percent.

TABLE III

| | | Catalyst Composition | | | | | Reaction Conditions | | | | |
|---|---|---|---|---|---|---|---|---|---|---|---|
| Example No. | Run No. | Cobalt Naphthenate mm | Tri-butyl Phosphine mm | Support g. | Base ml | Solvent ml | Catalyst Aged Hr. | Pressure psig | Temp. °C | H$_2$/Co | Reaction Time Hr. |
| X | 1 | 1.6 | 6.0 | 10 | — | 65 | 0 | 1355–700 | 147–170 | 1.2 | 1.5 |
| | 2 | <1.6 | <6.0 | 10 | — | 70 | 30 | 1445–910 | 127–159 | 1.0 | 3 |
| | 3 | 1.6 | 6.0 | 10 | — | dioxane 70 | 49 | 1400–1290 | 133–143 | 1.2 | 1 |
| | 4 | 1.6 | 6.0 | 10 | — | 65 | 54 | 1810–1410 | 153–160 | 2.5 | 3 |
| XI | 1 | 1.4 | 3.0 | 15 | — | C$_6$H$_6$ 70 | 0 | 1960–1010 | 141–173 | 1.0 | 2.7 |
| | 2 | <1.4 | <3.0 | 15 | — | | 70 | 120 | 2000–1100 | 141–180 | 1.0 | 1.3 |
| | 3 | 1.4 | 3.0 | 15 | — | | 70 | 144 | 1860–1020 | 156–174 | 1.2 | 1.5 |
| | 4 | 1.4 | 3.0 | 15 | Bu$_3$N 25 | | 55 | 149 | 1980–800 | 151–173 | 1.0 | 1.5 |
| | 5 | 1.4 | 3.0 | 15 | KOH 1 g | C$_6$H$_{11}$OH | | 168 | 1940–100 | 145–175 | 1.2 | 2.7 |
| XII | 1 | [Co(CO)$_3$(Bu$_3$P)]$_2$ 1.7 | | 15 | 0 | C$_6$H$_6$ | 80 | 0 | 1830–1340 | 107–174 | 1.0 | 2.5 |
| | 2 | <1.7 | | 15 | Bu$_3$N 15 | | 55 | 5 | 2120–1150 | 150–181 | 1.0 | 1.2 |
| | 3 | 1.7 | | 15 | — | | 50 | 24 | — | — | — | — |

TABLE IV

| | | | | | Product Distribution | | | | | | | |
|---|---|---|---|---|---|---|---|---|---|---|---|---|
| Example No. | Run No. | Feed g | Apparent Conversion % | n-Product* % | iC$_4$=O | nC$_4$=O | iC$_4$—OH | nC$_4$—OH | 2Et—C$_6$=O | 2Et-2-C$_6$=O | 2Et—C$_6$—OH | Unknown |
| | | | | | | | | Weight Percent | | | | |
| X | 1 | C$_3$=18.0 | 31 | 75 | 10.3 | 46.9 | 13.9 | 11.3 | 2.5 | 12.1 | trace | 3.4 |
| | 2 | C$_3$=22.0 | 18 | 88 | 11.6 | 40.7 | 1.5 | 9.2 | 2.5 | 29.7 | 0.6 | 4.0 |
| | 3 | C$_3$=20.0 | 13 | 82 | 11.8 | 60.3 | 5.4 | 12.0 | — | 7.1 | trace | 2.6 |
| | 4 | C$_3$=20.0 | 24 | 78 | 19.3 | 53.1 | 2.9 | 8.9 | 0.7 | 13.9 | trace | 1.2 |
| XI | 1 | C$_3$-20.0 | 22 | 81 | 12.2 | 24.6 | 7.0 | 7.7 | 3.6 | 37.5 | trace | 7.5 |
| | 2 | C$_3$-20.0 | 11 | 79 | 7.9 | 15.3 | 12.1 | 24.0 | 9.6 | 24.3 | trace | 6.8 |
| | 3 | C$_3$-20.0 | 22 | 71 | 25.8 | 33.6 | 2.2 | 6.2 | 2.6 | 26.4 | trace | 3.0 |
| | 4 | C$_3$-20.0 | 32 | 85 | 11.7 | 43.2 | 2.7 | 12.7 | 1.2 | 23.9 | trace | 4.6 |
| | 5 | C$_3$-20.0 | 60 | 87 | 7.4 | 20.7 | 3.0 | 7.2 | 8.0 | 26.8 | 4.3 | 22.7 |
| XII | 1 | C$_3$=20.0 | 17 | 67 | 25.4 | 13.0 | 3.5 | 4.1 | 6.9 | 35.5 | — | 11.8 |
| | 2 | C$_3$=20.0 | 43 | 87 | 9.1 | 41.7 | 3.6 | 13.3 | 7.9 | 21.0 | — | 3.3 |
| | 3 | CH$_2$=CH—CH$_2$—NH$_2$ | | | | | | | | | | |

*n-Products + product derived from n-products.

EXAMPLE XVIII

A homogeneous catalyst system was studied (in the absence of the support) to establish the basis of comparing with the results obtained from the previous solid catalyst systems. To a 300 cc autoclave a solution of 0.696 g [Co(CO)$_3$(Bu$_3$P)]$_2$ in 20 ml benzene, was charged along with 80 ml benzene. The reactor was rapidly closed under a nitrogen stream, and purged for a while. Propylene (20.3g) was fed and the reactor was pressured to 1200 psig with a premixed gas ($H_2/CO = 1:1$). After the system was slowly heated for an hour, the temperature and pressure of the reactor were 138° C. and 1650 psig. At this stage, the initial pressure drop was noted. The reaction was allowed to proceed under 1650°–1100 psig at 138°–180° C. for 40 minutes until it was quenched by running cold water through a cooling coil. About 93% of the feed was reacted to 21.5% isobutanal, 49.2% n-butanal, 4.7% iso-butanol, 15.3% n-butanol, 2.1% 2-ethylhexanol and 7.9% unidentified product.

EXAMPLE XIX

The interaction between cobalt carbonylphosphine complex ]$Co(CO)_3(Bu_3P)]_2$ and the support of this invention was studied under an atmosphere of hydrogen or nitrogen or air at ambient temperature. The complex, $[Co(CO)_3(Bu_3P)]_2$, which was synthesized by the method described before, was used throughout the present run. Microspheres of the support of Example III (5.0 g) and 30 ml of benzene were charged to a 100 ml Erlenmeyer flask stirred with a magnetic stirrer. The flask was stoppered with a serum cap and flushed with hydrogen to remove all traces of air. A dark red complex solution (1.0 mm $[Co(CO)_3(Bu_3P)]_2$ in 30 ml benzene) was injected to the system, and the system was stirred vigorously at room temperature for 2 hours. No apparent change was noted. However, when the system was exposed to air by removing the serum cap from the flask, the red complex turned rapidly to the bright blue solution within 10 minutes. The resulted blue species was gradually fixed on the base to leave a colorless supernatent liquid. The blue species was thought to be a mononucleus cobalt (II) complex.

The same experiment was repeated in the presence of an additional portion of tri-n-butylphosphine (3.0mm). There was no apparent change in the system for a relatively long period, even after the system was exposed to air. But, the system gradually turned to the bright blue color during an overnight period.

A dark red solution of $[Co(CO)_3(Bu_3P)]_2$ along in benzene (without the support) kept its stability against air a prolonged period (~30 hours). These experiments clearly indicate that the complex solution ($[Co(CO)_3$-$(Bu_3P)]_2$ solution (in benzene) is quite stable toward air and that the complex solution is stable even in the presence of the support if the system is under an inert atmosphere ($N_2$ or $H_2$).

A blank experiment was run in the absence of a cobalt component under the same condition employed for the hydroformylation of propylene. The liquid portion discharged from the reactor was analyzed by means of gas chromatographic techniques. No oxo product of propylene was found. This run clearly indicated that the phosphine interacts with the support in the absence of cobalt to be retained on the support under the hydroformylation conditions. It also indicated that an active catalytic center for the hydroformylation of propylene in the solid catalyst requires cobalt.

EXAMPLE XXI

A commercially available washed kaolin clay having the following composition, after removal of volatile materials:

| | | |
|---|---|---|
| $Al_2O_3$ | 46.3 | weight % |
| $SiO_2$ | 51.6 | weight % |
| $Na_2O$ | 1.61 | weight % |
| CuO | 0.28 | weight % |
| MgO | 0.21 | weight % | was formed into tablets in order to employ them as an effective supporting base. The clay was mixed with about 4% flake graphite, formed into tablets one-eighth inch diameter × one-sixteenth inch length, then cracked and sized to realize 8–14 (Tyler) mesh. Calcination consisted of heating in an electric muffle furnace using temperature programming to raise the temperature to 900° F. during 8 hours, and then holding for 6 hours. The support was then heated to about 1350° F. for 2 hours, and cooled in a desiccator.

A 300 cc autoclave equipped with a magnetic stirrer was used as a reactor in this work. Both 2.1 m. moles of cobalt naphthenate and 5.2 g of the clay tablets were charged in 50 ml of benzene in the reactor. These components were vigorously agitated under a hydrogen atmosphere at 100° F. for 45 minutes. After tri-n-butylphosphine (4.0 m. moles) was introduced to the reactor, 20 g. of propylene was fed and then the system was pressured from 150 psig to 660 psig with a premixed gas ($H_2/CO$ 1:1) and to 800 psig with hydrogen at 110° F. After about a 30 minute induction period, the pressure and temperature of reactor were 1070 psig and 220° F. An initial pressure drop was noticed at this stage. The exothermicity of the reaction was so great that the temperature of the reactor was raised from 220° F. to 274° F. within 5 minutes. As soon as the initial pressure drop was noticed, heating of the reactor was discontinued. The reactor was kept at 220°–274° F. for 30 minutes. The pressure dropped from 1070 psig to 500 psig during this period. The reaction was quenched by running cold water through a cooling coil in the reactor. An orange colored reaction mixture was discharged from the reactor. An apparent conversion of the propylene feed in this run was estimated to be 34%. The product distribution was 12.1% isobutanal, 41.6% n-butanal, 7.5% isobutanol, 24.1% n-butanol, and 14.8% unidentified products. Some of the catalyst species generated in the first run was removed in the discharged reaction mixture from the reactor. Apparently the amount of support charged in the reactor was not enough to support all the catalytic species in the system. The supported solid catalyst left inside of the reactor from the first run was washed twice with fresh portions of benzene. The washed catalyst was saved for four more consecutive batch runs over about a 92 hour period. Details of the results obtained in these runs are listed in Tables V and VI. The second run was started by feeding 20 g of propylene along with 20 ml benzene to the 2 hour aged catalyst. The system was pressured to 640 psig with a premixed gas ($H_2/Co$, 1:1) and then to 800 psig with hydrogen at 100° F. The heater was adjusted to raise the temperature of reactor from 100° F. to 260° F. within ~15 minutes. An initial pressure drop was noticed at the stage where the temperature and pressue were 260° F. and 1155 psig after about a 30 minute induction period. The reaction was allowed to proceed at 260°–286° F. for 1⅔ hours. During this period, temperature was raised by the exothermicity of the reaction and the pressure dropped from 1155 psig to 860 psig. A light orange colored reaction mixture was discharged from the reactor, and the product was analyzed by means of gas chromatographic techniques. The apparent conversion of the propylene feed was calculated to be 17%, and the product was composed of 14.2% isobutanal, 57.5% n-butanal, 3.8% isobutanol, 13.5% n-butanol, and 11.0% unidentified products. A noticeable decrease in the apparent conversion (from the first run to the second run) can be explained by the decrease of the catalyst concentration in the second run. Some of the catalyst species was removed from the reactor in the first run without being supported in the clay support. The same reaction was repeated in both the 3rd and 4th runs. In the fifth run, a fresh portion of tri-n-butylphosphine (3.0 m moles) was added to the catalyst aged for 92 hours from the four preceding runs. Propylene (20 g) in 30 ml benzene was introduced to the system, and the system was pressured from 100 psig to 600 psig a premixed gas ($H_2/CO$ 1:1) and then to 800 psig with hydrogen at 110° F. The reactor was heated slowly. It took about 2½ hours to raise the temperature of the reactor from 110° F. to 232° F. The initial pressure drop was observed when the system assumed 1190 psig and 232° F. The initial pressure drop was observed when the system assumed 1190 psig and 232° F. The reactor was kept at 232°–252° F. for 3½ hours. About 22% of the propylene feed was converted to give 14.3% isobutanal, 70.0% n-butanal, 2.0% isobutanol, 11.7% n-butanol, and 2.0% unidentified products. It is remarkable to maintain catalytic activity at the same level with the supported catalyst for about a 90 hour period. These results obtained in these runs clearly demonstrate that the clay support is quite effective to give an active supported solid catalyst for hydroformylation of olefins.

EXAMPLE XXII

This run was carried out in a homogeneous phase in order to study the role of the clay base for the hydroformylation of propylene. A homogeneous catalyst solution was prepared from 3.0 m moles cobalt (II) acetylacetonate and 9.0 m moles tri-n-butylphosphine in 50 ml decyl alcohol. Propylene (20 g) was allowed to react in the presence of the homogeneous catalyst solution under 1550–850 psig ($H_2/CO$ 1:1) at 275°–302° F. for an hour period. The feed was reacted in 28% conversion under these conditions. It is obvious from the data obtained from Example XXV and this Example that the clay is an effective promoter as well as a good base to support the catalytic species for the hydroformylaton of propylene. With the system in the presence of the clay base, propylene was reacted in higher conversion under milder conditions during much shorter reaction periods. Compare 1st runs, Example XXV and this Example.

TABLE V

| Ex. No. | Run No. | Co-Naph. m moles | Bu₃P | Base Clay g. | Solvent ml | Catalyst Aged hr. | Pressure psig | Temperature °F. | Reaction Time hr. | H₂/CO |
|---|---|---|---|---|---|---|---|---|---|---|
| XXI | 1st | 2.1 | 4.0 | 5.2 | C₆H₆ 50 | — | 1070–500 | 220–274 | ½ | 1.5 |
|  | 2nd | <2.1 | <4.0 | 5.2 | 20 | 2 | 1155–860 | 260–286 | 1⅔ | 1.5 |
|  | 3rd | <2.1 | <4.0 | 5.2 | 30 | 20 | 1110–875 | 238–260 | 3¼ | 1.5 |
|  | 4th | <2.1 | <4.0 | 5.2 | 38 | 69 | 1010–970 | 245–260 | 2 | 1 |
|  | 5th | <2.1 | Bu₃P +3.0 | 5.2 | 30 | 92 | 1190–750 | 232–252 | 3½ | 2.2 |
| XXII | — | Co(acac)₂ 3.0 | 9.0 | — | C₁₀OH 50 | — | 1550–850 | 275–302 | 1½ | 1 |

TABLE VI

| Ex. No. | Run No. | Feed g | Selectivity to Alc. & Ald. % | Conversion % | iC₄—Al Wt. % | n-C₄—Al Wt.% | iC₄—OH Wt.% | n-C₄—OH Wt. % | Un- known* Wt.% | 2Et C₆—OH Wt.% |
|---|---|---|---|---|---|---|---|---|---|---|
| XXI | 1st | C₃ = 20 | 85 | 34 | 12.1 | 41.6 | 7.5 | 24.1 | 14.8 | — |
|  | 2nd | C₃ = 20 | 88 | 17 | 14.2 | 57.5 | 3.8 | 13.5 | 11.0 | — |
|  | 3rd | C₃ = 20 | 88 | 21 | 22.4 | 54.5 | 3.0 | 9.2 | 10.9 | — |
|  | 4th | C₃ = 20 | 85 | 11 | 28.3 | 50.9 | 2.3 | 5.1 | 13.6 | — |
|  | 5th | C₃ = 20 | 98 | 22 | 14.3 | 70.0 | 2.0 | 11.7 | 2.0 | — |
| XXII | — | C₃ = 20 | 84 | 28 | 11.3 | 53.9 | 0.4 | 15.0 | 17.2 | 2.3 |

*Unknown + Heavy Product.

I claim:
1. In the process in which a batch of an olefin hydrocarbon of 2 to about 16 carbon atoms is hydroformylated by reaction with carbon monoxide and hydrogen in the presence of an excess of carbon monoxide and hydrogen in the presence of a catalyst comprising trialkylphosphine, each alkyl group being a lower alkyl, and cobalt, at a pressure within a range from 500 to 2500 psig at a temperature of from about 100° to about 350° C., the improvement which comprises conducting said hydroformylation in liquid phase in contact with a catalyst containing a major amount of calcined, sorptive, solid acidic aluminosiliceous support of about 45 to 95 weight per cent amorphous silica-alumina, and about 5 to 55 weight per cent alumina, the total alumina content of said support being about 20 to 70 weight per cent, the amount of cobalt being within the range from about 0.05 to about 0.6 weight per cent of the aluminosiliceous support, said support being prepared by mixing together a separate phase alumina hydrogel with a silica-alumina hydrogel, dewatering the mixture to provide a gel slurry of about 14 weight per cent solids, spray-drying said slurry, washing the spray-dried material, pelleting the washed material, and calcining the pellets at about 1350° F. for about 3 hours to provide calcined particles, said support containing less than 1.5 weight per cent sodium.

2. The process of claim 1 wherein said olefin is pentene-1.

3. The process of claim 1 wherein the hydroformylation is conducted in the presence of a molar ratio of trialkyl phosphine to cobalt which is significantly greater than unity.

4. The process of claim 1 wherein said olefin is pentene-1.

* * * * *